United States Patent
Thakur et al.

(10) Patent No.: US 8,602,996 B2
(45) Date of Patent: Dec. 10, 2013

(54) INTEGRATING DEVICE-BASED SENSORS AND BEDSIDE BIOMARKER ASSAYS TO DETECT WORSENING HEART FAILURE

(75) Inventors: Pramodsingh Hirasingh Thakur, White Bear Lake, MN (US); Abhilash Patangay, Inver Grove Heights, MN (US); Craig Stolen, New Brighton, MN (US); Timothy Meyer, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 211 days.

(21) Appl. No.: 13/118,932

(22) Filed: May 31, 2011

(65) Prior Publication Data

US 2011/0295084 A1    Dec. 1, 2011

Related U.S. Application Data

(60) Provisional application No. 61/350,065, filed on Jun. 1, 2010.

(51) Int. Cl.
*A61B 5/02*    (2006.01)

(52) U.S. Cl.
USPC .......................................... 600/483; 600/509

(58) Field of Classification Search
USPC .............................. 600/301, 509, 483; 435/7.1
See application file for complete search history.

(56) References Cited

U.S. PATENT DOCUMENTS

| | | | |
|---|---|---|---|
| RE39,816 E | 9/2007 | Stanton et al. | |
| 7,319,017 B2 | 1/2008 | Wagner | |
| 7,358,005 B2 | 4/2008 | Bourgeois | |
| 7,358,055 B2 | 4/2008 | Valkirs et al. | |
| 7,361,473 B2 | 4/2008 | Valkirs et al. | |
| 7,610,094 B2 | 10/2009 | Stahmann et al. | |
| 7,745,150 B2 | 6/2010 | Liang et al. | |
| 7,781,178 B2 | 8/2010 | Matsumori | |
| 2006/0155200 A1 | 7/2006 | Ng | |
| 2006/0258952 A1 | 11/2006 | Stahmann et al. | |
| 2006/0293609 A1 | 12/2006 | Stahmann et al. | |
| 2007/0270675 A1 | 11/2007 | Kane et al. | |

(Continued)

OTHER PUBLICATIONS

"Method and Apparatus for Improved Patient Management", IP.Com Technical Disclosure, Accession No. IPCOM000159365D, (Oct. 18, 2007), 5 pgs.

(Continued)

*Primary Examiner* — Tammie K Heller
(74) *Attorney, Agent, or Firm* — Schwegman Lundberg & Woessner, P.A.

(57) ABSTRACT

Devices and methods for improving the sensitivity and specificity of heart failure (HF) detection are described. The devices and methods can detect a HF status such as using physiological sensor data and external biomarker assays. An apparatus can comprise ambulatory physiological sensors that can provide a first HF status indicator and a second HF status indicator to a user. An external biomarker sensor can provide an amount of a biomarker present, such as an assay for B-type natriuretic peptide (BNP), which provides information about HF status. A processor circuit can switch from a first HF detection mode to a second detection mode such as in response to the information from the biomarker sensor. The first detection mode can detect HF status using the first HF status indicator, and the second detection mode can detect HF status using the second HF status indicator. The second detection mode can have a higher specificity than the first detection mode.

20 Claims, 2 Drawing Sheets

(56) References Cited

U.S. PATENT DOCUMENTS

| | | |
|---|---|---|
| 2008/0033260 A1* | 2/2008 | Sheppard et al. ............ 600/301 |
| 2009/0054741 A1 | 2/2009 | McAleer |
| 2009/0068677 A1 | 3/2009 | Matsumori |
| 2010/0030034 A1 | 2/2010 | Schulhauser et al. |
| 2010/0094102 A1 | 4/2010 | Zhang et al. |
| 2010/0203566 A1 | 8/2010 | Liang et al. |
| 2010/0285082 A1* | 11/2010 | Fernandez ................... 424/422 |

OTHER PUBLICATIONS

Ahmed, Ali, et al., "Diagnosis of heart failure in older adults: predictive value of dyspnea at rest.", Archives of Gerontology and Geriatrics, 38(3), (2004), 297-307.

Amellone, C., et al., "Intrathoracic Impedance Monitoring: Evaluations After Two-year Follow-up", HRS 2009 Meeting, (2009), Abstract PO05-143.

Battaglia, M., et al., "Accuracy of B-type natriuretic peptide tests to exclude congestive heart failure: systematic review of test accuracy studies", Arch Intern Med., 166(10), (May 22, 2006), 1073-80.

Braunwald, Eugene, "Biomarkers in Heart Failure", New England Journal of Medicine, 358, vol. 20, (May 15, 2008), 2148-59.

Collins, Sean P, et al., "The Combined Utility of an S3 Heart Sound and B-Type Natriuretic Peptide Levels in Emergency Department Patients with Dyspnea", Journal of Cardiac Failure, 12(4), (May 2006), 286-292.

Dieplinger, B., et al., "Evaluation of novel biomarkers for the diagnosis of acute destabilised heart failure in patients with shortness of breath", Heart, 95, (2009), 1508-1513.

Knackstedt, Christian, et al., "Integration of automatic intrathoracic fluid content measurement into clinical decision making in patients with congestive heart failure.", Pacing Clin Electrophysiol., 31(8), (Aug. 2008), 961-7.

Maisel, Alan, "Algorithms for Using B-Type Natriuretic Peptide Levels in the Diagnosis and Management of Congestive Heart Failure", Critical Pathways in Cardiology, 1(2), (2002), 67-73.

Maisel, Alan, et al., "Mid-region pro-hormone markers for diagnosis and prognosis in acute dyspnea: results from the BACH (Biomarkers in Acute Heart Failure) trial.", J Am Coll Cardiol., 55(19), (May 11, 2010), 2062-76.

Maisel, Alan S., et al., "Rapid measurement of B-type natriuretic peptide in the emergency diagnosis of heart failure", The New England Journal of Medicine, 347(3), (Jul. 18, 2002), 161-7.

Maisel, Alan, et al., "State of the art: using natriuretic peptide levels in clinical practice", European Journal of Heart Failure, 10(9), (2008), 824-839.

Matkovich, Scot J., et al., "Reciprocal regulation of myocardial microRNAs and messenger RNA in human cardiomyopathy and reversal of the microRNA signature by biomechanical support.", Circulation, 119(9), (Mar. 10, 2009), 1263-1271.

Michelucci, Antonio, et al., "Relation of Inflammatory Status to Major Adverse Cardiac Events and Reverse Remodeling in Patients Undergoing Cardiac Resynchronization Therapy", Journal of Cardiac Failure, 13(3), (Apr. 2007), 207-210.

Miller, Wayne L., et al., "Serial biomarker measurements in ambulatory patients with chronic heart failure: the importance of change over time", Circulation, 116(3), (Jul. 17, 2007), 249-57.

Milzman, D. P., et al., "ED Presentation of Dyspnea in HF Patients Results in Increased Hospital Stay and Medication Costs", Annals of Emergency Medicine, 46(3), [Abstract], (Sep. 2005), S38-S39.

Morrison, L. Katherine, et al., "Utility of a Rapid B-Natriuretic Peptide Assay in Differentiating Congestive Heart Failure from Lung Disease in Patients Presenting With Dyspnea", Journal of the American College of Cardiology, 39(2), (Jan. 16, 2002), 202-209.

Mulrow, C., et al., "Discriminating causes of dyspnea through clinical examination", J Gen Intern Med., 8(7), (Jul. 1993), 383-92.

Rocchiccioli, J. Paul, et al., "Biomarkers in heart failure: a clinical review", Heart Fail Rev., 15(4), (Jul. 2008), 251-73.

Schmitt, B. P, et al., "The diagnostic usefulness of the history of the patient with dyspnea", J Gen Intern Med., 1(6), (Nov.-Dec. 1986), 386-93.

Steinhart, Brian, et al., "Improving the diagnosis of acute heart failure using a validated prediction model", J Am Coll Cardiol., 54(16), (Oct. 13, 2009), 1515-21.

Swedberg, Karl, et al., "Guidelines for the diagnosis and treatment of chronic heart failure: executive summary (update 2005): The Task Force for the Diagnosis and Treatment of Chronic Heart Failure of the European Society of Cardiology", Eur Heart J., 26(11), (Jun. 2005), 1115-40.

Thygesen, Kristian, et al., "Recommendations for the use of natriuretic peptides in acute cardiac care: A position statement from the Study Group on Biomarkers in Cardiology of the ESC Working Group on Acute Cardiac Care", Eur Heart J., [Epub ahead of print], (Feb. 2, 2011), 9 pgs.

Tijsen, Anke J., et al., "MiR423-5p as a circulating biomarker for heart failure", Circulation Research, 106(6), (Apr. 2, 2010), 1035-9.

Wang, Ru-Xing, et al., "BNP/NT-proBNP and cardiac pacing: a review", Pacing Clin Electrophysiol., 32(6), (Jun. 2009), 794-9.

Ypenburg, C., et al., "Intrathoracic impedance monitoring to predict decompensated heart failure", Am J Cardiol., 99(4), (Feb. 15, 2007), 554-7.

Yu, C. M, et al., "Intrathoracic impedance monitoring in patients with heart failure: correlation with fluid status and feasibility of early warning preceding hospitalization", Circulation, 112(6), (Aug. 9, 2005), 841-8.

"International Application Serial No. PCT/US2011/038514, International Search Report mailed Aug. 19, 2011", 6 pgs.

"International Application Serial No. PCT/US2011/038514, Written Opinion mailed Aug. 19, 2011", 7 pgs.

Maisel, Alan S., et al., "Acoustic cardiography S3 detection use in problematic subgroups and B-type natriuretic peptide "gray zone": secondary results from the Heart failure and Audicor technology for Rapid Diagnosis and Initial Treatment Multinational Investigation", American Journal of Emergency Medicine 29 (8), (Oct. 2011), 924-931.

Zuber, Michel, "Usefulness of Acoustic Cardiography to Resolve Ambiguous Valves of B-Type Natriuretic Peptide Levels in Patients with Suspected Heart Failure", The American Journal of Cardiology 100 (5), (Sep. 1, 2007), 866-869.

* cited by examiner

INTEGRATING DEVICE-BASED SENSORS AND BEDSIDE BIOMARKER ASSAYS TO DETECT WORSENING HEART FAILURE

CROSS-REFERENCE TO RELATED APPLICATIONS

This application claims the benefit of U.S. Provisional Application No. 61/350,065, filed on Jun. 1, 2010, under 35 U.S.C. §119(e), which is incorporated herein by reference in its entirety.

BACKGROUND

Cardiac rhythm management (CRM) devices include implantable or ambulatory devices such as pacemakers, cardioverter defibrillators, and devices that provide a combination of pacing and defibrillation, including cardiac resynchronization therapy. The devices can be used to detect worsening heart failure through internal monitoring of a patient's condition, as well as to treat patients using electrical therapy. The devices can include electrical leads in communication with sense amplifiers to monitor electrical heart activity within a patient, and often include sensors to monitor other internal patient parameters.

Biomarker assays, such as B-type natriuretic peptide (BNP), can also be used to detect worsening heart failure. BNP is a polypeptide secreted by the ventricles of the heart in response to excessive stretching of cardiomyocytes. BNP is co-secreted with an amino acid called NT-proBNP, which is biologically inactive. Both BNP and NT-proBNP levels in the blood can be used for screening and diagnosis of heart failure, and can also be useful to establish prognosis in heart failure, as both biomarkers are typically higher in patients with worse outcome.

OVERVIEW

This document describes, among other things, an apparatus and method in which physiological sensor data can be combined with external biomarker assays, such as a bedside assay for B-type natriuretic peptide (BNP), to improve the sensitivity and specificity of heart failure detection.

Example 1 can include subject matter that can include an apparatus comprising: at least one ambulatory physiological sensor configured to provide a first heart failure status indicator and a second heart failure status indicator to a user or automated process; an external biomarker sensor, configured to provide information to the user or automated process about an amount of a biomarker present in a biological substance, wherein the amount of the biomarker present provides information about heart failure status; and a processor circuit, communicatively coupled to the at least one ambulatory physiological sensor and the external biomarker sensor, the processor configured to switch, in response to information from the biomarker sensor, from a first heart failure status detection mode to a higher specificity second heart failure status detection mode detecting heart failure status using a change over time in the second heart failure status indicator.

In Example 2, the subject matter of Example 1 can optionally include the processor configured to use the amount of the biomarker present to adjust a specified threshold value of the second heart failure status indicator.

In Example 3, the subject matter of any one of Examples 1-2 can optionally include the processor configured to use the amount of the biomarker present to adjust a specified threshold value of at least one of the first or second heart failure status indicators.

In Example 4, the subject matter of any one of Examples 1-3 can optionally include the physiological sensor including at least one of a respiration sensor or a thoracic fluid sensor, wherein the first heart failure status indicator includes at least one of a measure of respiration or a measure of thoracic fluid.

In Example 5, the subject matter of any one of Examples 1-4 can optionally include the physiological sensor including a heart sound sensor, wherein the second heart failure status indicator includes a measure of a S3 heart sound.

In Example 6, the subject matter of any one of Examples 1-5 can optionally include the biomarker including at least one of BNP, NT-proBNP, ANP, MR-proANP, adrenomedullin, ST2, serum sodium, copeptin, CT-proET-1, adiponectin, 15 chromogranin A, proguanylin, prouroguanylin, hsTropinin-I, Corin, Urotensin, IL-6, hsCRP, miR423-5p, miR129-5p, miR1254, HS__202.1, and miR622.

In Example 7, the subject matter of any one of Examples 1-6 can optionally include the processor configured to switch from the first heart failure status detection mode to the higher specificity second heart failure status detection mode when the amount of biomarker present is within a specified threshold range.

In Example 8, the subject matter of any one of Examples 1-7 can optionally include the processor, when in the first heart failure status detection mode, configured to use information about the first heart failure status indicator and the amount of biomarker present to provide information about heart failure status.

In Example 9, the subject matter of any one of Examples 1-8 can optionally include the processor, when in the first heart failure status detection mode, configured to provide an alert to the user or automated process when the amount of biomarker present exceeds a specified threshold value.

In Example 10, the subject matter of any one of Examples 1-9 can optionally include the processor, when in the second heart failure status detection mode, configured to use information about the first heart failure status indicator, the amount of biomarker present, and a change over time in the second heart failure status indicator to provide information about heart failure status.

In Example 11, the subject matter of any one of Examples 1-10 can optionally include the processor, when in the second heart failure status detection mode, configured to provide an alert to the a user or automated process when the second heart failure status indicator exceeds a specified threshold value.

In Example 12, the subject matter of any one of Examples 1-11 can optionally include the apparatus being implantable.

Example 13 can include, or can optionally be combined with any one of Examples 1-12 to include subject matter that can include using at least one ambulatory physiological sensor for providing a first heart failure status indicator and a second heart failure status indicator; using an external biomarker sensor, detecting an amount of a biomarker present in a biological substance to provide information about heart failure status; using information about the amount of biomarker present, switching from a first heart failure status detection mode to a higher specificity second heart failure status detection mode detecting heart failure status using a change over time in the second heart failure status indicator.

In Example 14, the subject matter of any one of Examples 1-13 can optionally include using the amount of the biomarker present to adjust a specified threshold value of at least one of the first or second heart failure status indicators.

In Example 15, the subject matter of any one of Examples 1-14 can optionally include the physiological sensor including at least one of a respiration sensor or a thoracic fluid sensor, wherein the first heart failure status indicator includes at least one of a measure of respiration or a measure of thoracic fluid.

In Example 16, the subject matter of any one of Examples 1-15 can optionally include the physiological sensor including a heart sound sensor, wherein the second heart failure status indicator includes a measure of a S3 heart sound.

In Example 17, the subject matter of any one of Examples 1-16 can optionally include the biomarker including at least one of BNP, NT-proBNP, ANP, MR-proANP, adrenomedullin, ST2, serum sodium, copeptin, CT-proET-1, adiponectin, 15 chromogranin A, proguanylin, prouroguanylin, hsTroponin-I, Corin, Urotensin, IL-6, hsCRP, miR423-5p, miR129-5p, miR1254, HS_202.1, and miR622.

In Example 18, the subject matter of any one of Examples 1-17 can optionally include providing an alert to the user or automated process when the amount of biomarker present exceeds a specified threshold value.

In Example 19, the subject matter of any one of Examples 1-18 can optionally include providing an alert to the user or automated process when the second heart failure status indicator exceeds a specified threshold value.

In Example 20, the subject matter of any one of Examples 1-19 can optionally include a device-readable medium including instructions that, when performed by the device, comprise: using at least one ambulatory physiological sensor for providing a first heart failure status indicator and a second heart failure status indicator; using an external biomarker sensor, detecting an amount of a biomarker present in a biological substance to provide information about heart failure status; and using information about the amount of biomarker present, switching from a first heart failure status detection mode to a higher specificity second heart failure status detection mode detecting heart failure status using a change over time in the second heart failure status indicator.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that device-based sensors and external biomarker assays can be integrated to improve detection of worsening heart failure. Changing levels of biomarkers, such as BNP, can be shown to have good specificity and sensitivity in predicting and detecting worsening heart failure. However, assaying for BNP can only be done intermittently since it requires a blood test. On the other hand, sensors included within CRM devices, such as respiration or impedance sensors, can monitor a patient's condition chronically. While such sensors can be highly sensitive for detecting worsening heart failure, they may not be capable of matching the specificity of biomarkers. Thus, a fusion technique integrating device-based sensors and bedside biomarker assays in a sequential fashion can be used to improve the sensitivity and specificity of heart failure detection without the need for frequent blood tests.

Figure 1:
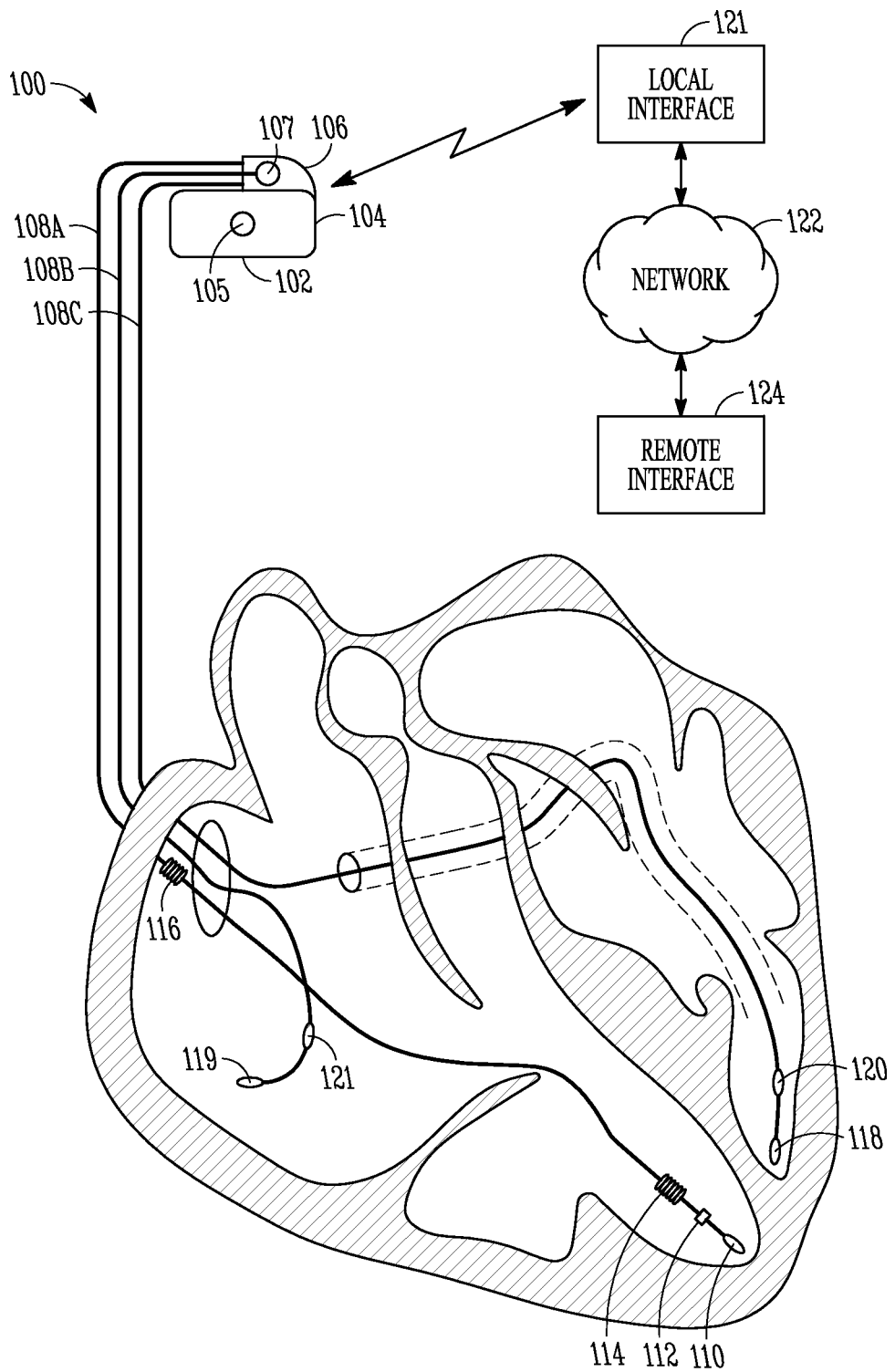
FIG. 1 is a schematic diagram illustrating generally an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular CS/LV lead 108C can extend from the SVC into the RA, through a coronary sinus (CS) into the coronary vasculature, such as near a portion of a left ventricle (LV). In an example, this second CS/LV lead 108B can include at least a distal electrode 118 and a proximal electrode 120, from which electrostimulation energies can be delivered or intrinsic electrical heart signals can be sensed. An intravascular right atrial (RA) lead 108B can extend from the SVC into the RA, and can include a distal electrode 119 and a proximal electrode 121. Other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

In an example, implantable CRM device 100 can use such a communication circuit to communicate with an external device, such as an external biomarker sensor (not shown). An illustrative example can include communicating between an implantable CRM device 100 and an external biomarker sensor, such as by using the Boston Scientific Corp. (Cardiac Pacemakers, Inc.) LATITUDE® System, which can automatically collect information from a subject's implantable CRM device 100 and communicate the information to the external biomarker sensor, such as via local interface 121 that can be communicatively coupled via a communication network 122 to remote interface 124.

Figure 2:
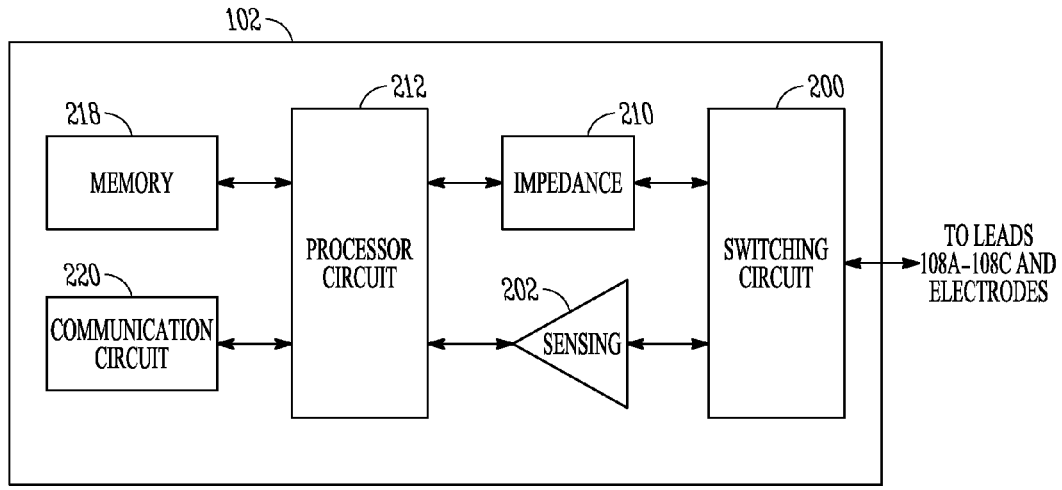
FIG. 2 is a block diagram illustrating generally an example of portions of the CRM device electronics unit.

FIG. 2 shows an example of portions of the CRM device electronics unit 102. In an example, this can include a switching circuit 200, such as for selectively connecting to the various electrodes such as on the leads 108A-C or elsewhere. A sensing circuit 202 can be selectively coupled to various electrodes by the switching circuit 200, and can include sense amplifiers, filter circuits, other circuits such as for sensing intrinsic electrical signals, such as intrinsic heart signals. An impedance measurement circuit 210 can be selectively coupled to various electrodes by the switching circuit 200, such as for measuring a lead impedance, a tissue impedance, a regional or organ impedance, or other impedance. Impedance measurements, such as intrathoracic impedance measurements, can be used, for example, to detect a respiration signal, which can include information such as respiration rate, respiration depth, or a respiration morphological pattern. Such intrathoracic impedance measurements can also be used to detect a fluid status. In an example, the sensing circuit 202 and the impedance measurement circuit 210 can be coupled to a processor circuit 212. In an example, the processor 212 can perform instructions, such as for signal processing of signals derived by the sensing circuit 202 or the impedance circuit 210, or for controlling operation of other operations of the CRM device 100. The processor 212 can be coupled to or include a memory circuit 218, such as for storing or retrieving instructions or data, or a communication circuit 220, such as for communicating with the local interface 121.

Figure 3:
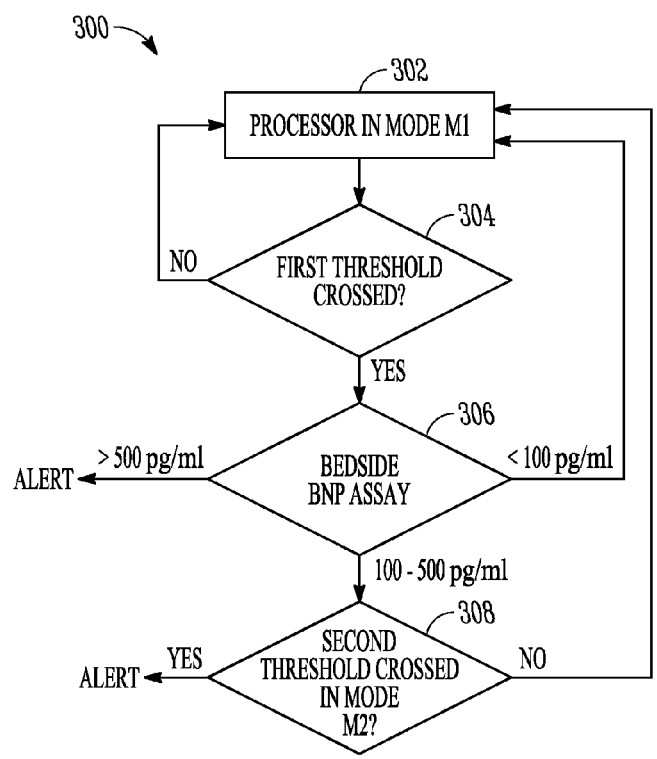
FIG. 3 illustrates an example of integrating device-based sensors and biomarker assays to detect worsening heart failure.

FIG. 3 illustrates an example of a method 300 of integrating device-based sensors and biomarker assays to detect worsening heart failure. At 302, the processor 212 can run in mode M1. Mode M1 is a higher sensitivity heart failure status detection mode, in which at least one ambulatory physiological sensor, such as CRM device 100, can be configured to provide a first heart failure status indicator having a higher sensitivity than another second heart failure status indicator that can be obtained when the processor 212 is running in another mode other than mode M1. In an example, the at least one ambulatory physiological sensor can be implanted within the patient's body as an internal sensor. In other examples, the physiological sensor can adhere to a patient's skin, can be worn against a patient's skin, or can comprise an ambulatory external sensor. In some examples, the physiological sensor can include both internal and external sensing components. The higher sensitivity heart failure status indicator can be provided to a user or automated process. In an example, the higher sensitivity heart failure status indicator can be obtained from impedance measurement circuit 210. In an example, other higher sensitivity device-based sensors can be used, in addition to or instead of an impedance sensor.

In an example, impedance measurement circuit 210 can be used as a respiration sensor to detect dyspnea, a common symptom in patients hospitalized for heart failure exacerbation. Although dyspnea can be shown to be a highly sensitive marker for worsening heart failure, having a sensitivity of about 92%, the specificity of dyspnea as symptom of heart failure can be shown to be only about 19% (See, e.g., Ahmed A, et al. Diagnosis of heart failure in older adults: predictive value of dyspnea at rest. *Archive of Gerontology and Geriatrics.* 2004; 28(3):297-307). The two chief causes of dyspnea, heart failure and lung disease, can be difficult to differentiate, accounting for the low specificity of dyspnea as a heart failure status indicator.

Other measures of respiration that can be used to detect worsening heart failure, in addition to or instead of dyspnea, include continuous measures such as tidal volume, respiratory rate, and minute ventilation, for example. Abnormal breathing conditions based on the above measures include apnea (e.g., tidal volume is close to zero), hypopnea (e.g., tidal volume is reduced by 30%), tachypnea (e.g., increased respiratory rate), and rapid shallow breathing (e.g., increased respiratory rate and reduced tidal volume). Such abnormal breathing conditions can be indicative of worsening heart failure. The prevalence of such conditions can be quantified using indices such as the apnea-hypopnea index, the respiratory-disturbance index, and the rapid shallow breathing index, for example.

In an example, impedance measurement circuit 210 can additionally be used to detect thoracic fluid, which can be used to detect pulmonary congestion associated with worsening heart failure. An example of a measure of thoracic fluid includes intrathoracic impedance. Intrathoracic impedance can be shown to have moderate sensitivity (60%) and specificity (73%) as a heart failure status indicator (See, e.g., Ypenburg C, et al. Intrathoracic impedance monitoring to predict decompensated heart failure. *Am J. Cardiol.* 2007 Feb. 15: 99(4):554-7). At 304, it can be determined whether the higher sensitivity heart failure status indicator (e.g., dyspnea or intrathoracic impedance) has crossed a first specified threshold value. If the first specified threshold value has not been crossed, the process reverts to 302 and the processor continues to operate in mode M1. If, however, the first specified threshold value has been crossed, the process flows to 306, where a biomarker assay, such as a bedside BNP assay, can be performed. BNP can be shown to have a high sensitivity (87%) and a high specificity (72%) for detection of worsening heart failure (See. e.g., Battaglia et al. Accuracy of B-type natriuretic peptide tests to exclude congestive heart failure. *Archives of Internal Medicine.* 2006; 166: 1073-1080). Bedside BNP assays require a patient's blood to be drawn and assayed. Because of the high specificity of BNP, this test can be used to screen out false positives obtained from the higher sensitivity device-based sensor. Thus, the sensitivity-specificity of the device-based sensor can be improved by the addition of a BNP assay when indicated. However, unnecessary blood draws can be avoided by only performing the BNP assay when the higher sensitivity heart failure status indicator has crossed the first specified threshold value.

Other biomarker assays can be used in addition to or in place of BNP. Biomarkers can include an amount, relative amount, concentration, or relative concentration of a biological substance—such as a protein, peptide, amino acid, electrolyte, chemical, nucleic acid, or hormone, for example— that can be found in a tissue or fluid of the human body (e.g., blood, urine, saliva, mucus, semen, sweat, tears, sebum, or other bodily secretions). Examples of biomarkers that can be used in addition to or in place of BNP include NT-proBNP, A-type natriuretic peptide (ANP), midregional pro-A-type natriuretic peptide (MR-proANP), adrenomedullin, midregional pro-Adrenomedullin (MR-proADM), the soluble isoform of a interleukin-1 receptor family member ST2 (sST2), serum sodium concentration, the C-terminal part of the arginine vasopressin prohormone (copeptin), chromogranin A and the C-terminal endothelin-1 precursor fragment (CT-proET-1), adiponectin, chromogranin A, proguanylin, prouroguanylin, hsTroponin-I, corin, urotensin, interleukin-6 (IL-6), and c-reactive protein (hsCRP), microRNA miR423-5p, microRNA miR129-5p, microRNA miR1254, microRNA HS_202.1, and microRNA miR622. Combinations of biomarkers markers can also be used in order to achieve a desired sensitivity and/or specificity.

Studies have shown that when a patient's BNP level is below 100 pg/ml, the negative predictive value for worsening heart failure is 89%. However, when a patient's BNP level is above 400-500 pg/ml, the positive predictive value for worsening heart failure is greater than 90%. BNP values between 100 pg/ml and 500 pg/ml fall into a "gray zone," requiring further examination and diagnostic testing to predict the likelihood of worsening heart failure (See, e.g., Collins et al. The combined utility of an S3 heart sound and B-type natriuretic peptide levels in emergency department patients with dyspnea. *J Cardiac Fail.* 2006; 12(4):286-92). Thus, at 306, when BNP is less than 100 pg/ml, worsening heart failure can be ruled out, and the process reverts to 302 where the processor 212 continues to operate in mode M1. When, at 306, BNP is greater than 500 pg/ml, then an alert or alarm can be issued to the patient, healthcare provider, or an automated system, indicating that the patient has worsening heart failure and may require hospitalization. Examples of alerts or alarms include audible alarms associated with CRM device 100, audible alarms or visual displays of alert on the LATITUDE® communicator installed at a patient's home, or an alert flag sent to the LATITUDE® server. However, if BNP is between 100 and 500 pg/ml at 306, the process flows to 308, where the processor 212 switches from mode M1 to mode M2.

In some examples, when other biomarker assays are used in addition to or in place of BNP, marker thresholds are set in a manner similar to that described above for BNP. In some examples, a patient's biomarker threshold levels are set such that a negative predictive value for worsening heart failure is greater than 89% and a positive predictive value for worsening heart failure is greater than 90%. Biomarker values between the threshold levels fall into a "gray zone," requiring further examination and diagnostic testing to predict the likelihood of worsening heart failure.

In an example, for Nt-proBNP, a level of less than 300 pg/ml rules out worsening heart failure, and a level of greater than 900 pg/ml indicates that the patient has worsening heart failure. (See, e.g., *Journal of the American College of Cardiology*, Volume 54, Issue 16, 13 Oct. 2009, Pages 1515-1521). In another example, threshold levels are age-dependent. For instance, for Nt-proBNP, an indication that a patient has worsening heart failure includes a level of greater than 450 pg/ml in a patient less than 50 years old, a level of greater than 900 pg/ml in a patient 50-75 years old, and a level greater than 1800 pg/ml in a patient greater than 75 years old. (See, e.g., Thygesen et al., Recommendations for the use of natriuretic peptides in acute cardiac care. *European Heart Journal*, 2011, 9 pages). In another example, for MR-proADM, a level of less than 130 pmol/l rules out worsening heart failure, and a level of greater than 338 pmol/l indicates that the patient has worsening heart failure. (See, e.g., Journal of the American College of Cardiology Volume 55, Issue 19, 11 May 2010, Pages 2062-2076).

Mode M2 is a higher specificity mode in which at least one ambulatory physiological sensor, such as CRM device 100, can be configured to provide a second heart failure status indicator having a higher specificity than the first heart failure status indicator obtained when the processor 212 is running in another mode other than mode M2 (e.g., mode M1). In an example, the at least one ambulatory physiological sensor can be implanted within the patient's body as an internal sensor. In other examples, the physiological sensor can adhere to a patient's skin, can be worn against a patient's skin, or can comprise an ambulatory external sensor. In some examples, the physiological sensor can include both internal and external sensing components. The higher specificity heart failure status indicator can be provided to a user or automated process. In an example, the higher specificity heart failure status indicator can be obtained from a heart sound sensor, such as included within sensing circuit 202. The heart sound sensor can be configured to detect a S3 heart sound, for example. In an example, mode M2 can include the integration of multiple higher specificity sensors. Such higher specificity sensors can be used to improve the specificity of heart failure detection when BNP is in the gray zone (e.g., 100-500 pg/ml). For example, studies have shown that when BNP is between 100 pg/ml and 500 pg/ml, the positive predictive value for heart failure based on BNP alone is 54%. When a BNP measurement in this range is combined with the presence of an audible S3 heart sound, however, the positive predictive value for heart failure is 80% (See, e.g., Collins et al.).

At 308, it can be determined whether a second specified threshold value is crossed when the processor 212 is running in mode M2. In an example, the second specified threshold value can be a specified change in the amplitude of an S3 heart sound over time. For example, at 308, a 20% change in amplitude of the S3 heart sound over a short-term period (e.g., 3 days) or a long-term period (e.g., 30 days) can be used as the second specified threshold value. When the second specified threshold value is crossed, an alert or alarm can be issued to the patient, healthcare provider, or an automated system, indicating that the patient has worsening heart failure and may require hospitalization. When the second specified threshold value is not crossed, the process reverts back to 302 where the processor 212 operates in mode M1.

In an example, the first specified threshold value, used when the processor 212 is operating in the higher sensitivity mode M1 (e.g., a specified respiration or intrathoracic impedance measurement value), can be determined or modified based on a patient's BNP level. For example, at least one ambulatory physiological sensor, such as CRM device 100, can be configured to track the number of times a patient's BNP value is less than 100 pg/ml (e.g., count 1) and the number of times the patient's BNP value is greater than 100 pg/ml (e.g., count 2) over a specified period of time, such as over the previous six months. If count 1 is substantially higher than count 2 (e.g., if count 1 exceeds count 2 by a specified threshold value), it can be concluded that the first specified threshold value, used while the processor 212 is operating in the higher sensitivity mode M1, is too low and should be increased. On the other hand, if count 2 is substantially higher than count 1 (e.g., if count 2 exceeds count 1 by a specified threshold value), it can be concluded that the first specified threshold value in the higher sensitivity mode M1 is too high and should be decreased. In an example, CRM device 100 can be configured to automatically adjust the first specified threshold value in the higher sensitivity mode M1 based on count 1 and count 2.

In an example, the first specified threshold value, used when the processor 212 is operating in the higher sensitivity mode M1, can be adjusted based on whether or not the above described method results in a correct identification of heart failure. The determination of whether or not the method results in a correct identification of heart failure can be based on the patient's BNP level (e.g., if heart failure has been identified in a patient who has a BNP value of less than 100 pg/ml, the heart failure identification can be incorrect), or input of the physician or other health care provider. In an example, the physician or health care provider can adjust the first specified threshold value based on a patient's BNP level. For example, if an alert is issued indicating that the patient has worsening heart failure, and the physician determines that the alert is a false positive based on the patient's BNP level, the physician can adjust, or cause CRM device 100 to automatically adjust, the first specified threshold value. In addition, the physician can use data stored by CRM device 100 (e.g., number of alerts issued and patient's BNP level at time of issuance) to adjust the first specified threshold during routine follow-up visits.

In an example, the second specified threshold value, used when the processor is operating in mode M2 (e.g., a specified percentage of change in S3 amplitude over time), can be determined or modified based on a patient's BNP level. For example, if a patient's BNP is in the gray zone (e.g., 100-500 pg/ml), the gray zone can be further categorized into a "low" gray zone (e.g., 100-233 pg/ml), a "medium" gray zone (e.g., 234-366 pg/ml), and a "high" gray zone (e.g., 367-500 pg/ml). The S3 change threshold can then be set to a "large," "medium," or "small" change in S3, corresponding to the "low," "medium," and "high" BNP gray zones, respectively. In an example, a "large" S3 change threshold can be 4 mG, and a "small" S3 change threshold can be 1 mG. In other words, when a patient's BNP is in the "low" gray zone (e.g., 100-233 pg/ml), the S3 change threshold can be required to be "large" (e.g., the change in S3 amplitude must at least 4 mG) in order to trigger an alert or alarm indicating worsening heart failure. Similarly, when a patient's BNP is in the "high" gray zone (e.g., 367-500 pg/ml), the S3 change threshold can be required to be "small" (e.g., the change in S3 amplitude need only be 1 mG) in order to trigger an alert or alarm indicating worsening heart failure.

In an example, the same set of sensors can be combined differentially for use in either the higher sensitivity mode M1 or the higher specificity mode M2. In mode M1, only one of the sensors can be required to cross a specified threshold in order to trigger an alarm or alert. In mode M2, all of the sensors can be required to cross a specified threshold in order to trigger an alarm or alert.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
two or more ambulatory physiological sensors configured to provide, to a user or automated process, a first heart failure status indicator using a first sensor selected from the two or more ambulatory physiological sensors and a second heart failure status indicator using a second sensor selected from the two or more ambulatory physiological sensors, the second sensor different from the first sensor;
an external biomarker sensor, configured to provide information to the user or automated process about an amount of a biomarker present in a biological substance, wherein the amount of the biomarker present provides information about heart failure status; and
a processor circuit, communicatively coupled to the at least one ambulatory physiological sensor and the external biomarker sensor, the processor configured to switch, in response to information from the biomarker sensor, from a first heart failure status detection mode detecting heart failure status using the first heart failure status indicator to a second heart failure status detection mode detecting heart failure status using a change over time in the second heart failure status indicator, the second heart failure status detection mode different from and having a higher specificity than the first heart failure status detection mode.

2. The apparatus of claim 1, wherein the processor is configured to use the amount of the biomarker present to adjust a specified threshold value of the second heart failure status indicator.

3. The apparatus of claim 1, wherein the processor is configured to use the amount of the biomarker present to adjust a specified threshold value of at least one of the first or second heart failure status indicators.

4. The apparatus of claim 1, wherein the physiological sensor includes at least one of a respiration sensor or a thoracic fluid sensor, and wherein the first heart failure status indicator includes at least one of a measure of respiration or a measure of thoracic fluid.

5. The apparatus of claim 1, wherein the physiological sensor includes a heart sound sensor, and wherein the second heart failure status indicator includes a measure of a S3 heart sound.

6. The apparatus of claim 1, wherein the biomarker includes at least one of BNP, NT-proBNP, ANP, MR-proANP, adrenomedullin, ST2, serum sodium, copeptin, CT-proET-1, adiponectin, 15 chromogranin A, proguanylin, prouroguanylin, hsTropinin-I, Corin, Urotensin, IL-6, hsCRP, miR423-5p, miR129-5p, miR1254, HS_202.1, and miR622.

7. The apparatus of claim 1, wherein the processor is configured to switch from the first heart failure status detection mode to the higher specificity second heart failure status detection mode when the amount of biomarker present is within a specified threshold range.

8. The apparatus of claim 1, wherein the processor, when in the first heart failure status detection mode, is configured to use information about the first heart failure status indicator and the amount of biomarker present to provide information about heart failure status.

9. The apparatus of claim 8, wherein, the processor, when in the first heart failure status detection mode, is configured to provide an alert to the user or automated process when the amount of biomarker present exceeds a specified threshold value.

10. The apparatus of claim 1, wherein the processor, when in the second heart failure status detection mode, is configured to use information about the first heart failure status indicator, the amount of biomarker present, and a change over time in the second heart failure status indicator to provide information about heart failure status.

11. The apparatus of claim 10, wherein the processor, when in the second heart failure status detection mode, is configured to provide an alert to the a user or automated process when the second heart failure status indicator exceeds a specified threshold value.

12. The apparatus of claim 1, wherein the second heart failure status indicator includes an integration of measures from multiple physiological sensors.

13. A method comprising:
using at least one two or more ambulatory physiological sensors for providing a first heart failure status indicator using a first sensor selected from the two or more ambulatory physiological sensors and a second heart failure status indicator using a second sensor selected from the two or more ambulatory physiological sensors, the second sensor different from the first sensor;
using an external biomarker sensor, detecting an amount of a biomarker present in a biological substance to provide information about heart failure status;
using information about the amount of biomarker present, switching from a first heart failure status detection mode detecting heart failure status using the first heart failure status indicator to a second heart failure status detection mode detecting heart failure status using a change over time in the second heart failure status indicator, the second heart failure status detection mode different from and having a higher specificity than the first heart failure status detection mode.

14. The method of claim 13, comprising using the amount of the biomarker present to adjust a specified threshold value of at least one of the first or second heart failure status indicators.

15. The method of claim 13, wherein the physiological sensor includes at least one of a respiration sensor or a thoracic fluid sensor, and wherein the first heart failure status indicator includes at least one of a measure of respiration or a measure of thoracic fluid.

16. The method of claim 13, wherein the physiological sensor includes a heart sound sensor, and wherein the second heart failure status indicator includes a measure of a S3 heart sound.

17. The method of claim 13, wherein the biomarker includes at least one of BNP, NT-proBNP, ANP, MR-proANP, adrenomedullin, ST2, serum sodium, copeptin, CT-proET-1, adiponectin, 15 chromogranin A, proguanylin, prouroguanylin, hsTropinin-I, Corin, Urotensin, IL-6, hsCRP, miR423-5p, miR129-5p, miR1254, HS_202.1, and miR622.

18. The method of claim 13, comprising providing an alert to the user or automated process when the amount of biomarker present exceeds a specified threshold value.

19. The method of claim 13, comprising providing an alert to the user or automated process when the second heart failure status indicator exceeds a specified threshold value.

20. A non-transitory device-readable medium including instructions that, when performed by a device, comprise:
using two or more ambulatory physiological sensors for providing a first heart failure status indicator using a first sensor selected from the two or more ambulatory physiological sensors and a second heart failure status indicator using a second sensor selected from the two or more ambulatory physiological sensors, the second sensor different from the first sensor;
using an external biomarker sensor, detecting an amount of a biomarker present in a biological substance to provide information about heart failure status; and
using information about the amount of biomarker present, switching from a first heart failure status detection mode detecting heart failure status using the first heart failure status indicator to a second heart failure status detection mode detecting heart failure status using a change over time in the second heart failure status indicator, the second heart failure status detection mode different from and having a higher specificity than the first heart failure status detection mode.

* * * * *